United States Patent
Smail et al.

(10) Patent No.: US 6,553,852 B1
(45) Date of Patent: Apr. 29, 2003

(54) APPARATUS AND PROCESS FOR AN OFF-SURFACE CONE PENETROMETER SENSOR

(75) Inventors: Timothy R. Smail, Augusta, GA (US); Phillip J. French, Evans, GA (US); Russell K. Huffman, Martinez, GA (US)

(73) Assignee: Westinghouse Savannah River Company, L.L.C., Aiken, SC (US)

( * ) Notice: Subject to any disclaimer, the term of this patent is extended or adjusted under 35 U.S.C. 154(b) by 177 days.

(21) Appl. No.: 09/672,601

(22) Filed: Sep. 29, 2000

Related U.S. Application Data

(60) Provisional application No. 60/160,975, filed on Oct. 22, 1999.

(51) Int. Cl.[7] ............................................. G01N 1/00
(52) U.S. Cl. ............................................. 73/866.5
(58) Field of Search ................. 73/78, 84, 784, 73/864.74, 866.5; 374/208, 155; 324/696, 694; 33/544.2, 544.3

(56) References Cited

U.S. PATENT DOCUMENTS

| | | | |
|---|---|---|---|
| 2,686,690 A | | 8/1954 | Kushnir |
| 2,815,578 A | * | 12/1957 | Broussard .................. 33/544.3 |
| 2,860,586 A | | 11/1958 | Nozell |
| 2,865,315 A | | 12/1958 | Goldstein |
| 3,175,392 A | * | 3/1965 | Tharalson et al. ............. 175/50 |
| 3,466,926 A | * | 9/1969 | Ruppeneit et al. ......... 33/544.2 |
| 3,469,639 A | | 9/1969 | Charlade |
| 3,596,719 A | | 8/1971 | Koziski |
| 3,690,166 A | * | 9/1972 | Grice et al. .................... 175/41 |
| 4,038,875 A | | 8/1977 | Walkotten |
| 4,445,788 A | * | 5/1984 | Twersky et al. ........... 73/866.5 |
| 4,461,171 A | | 7/1984 | de la Cruz |
| 4,848,484 A | | 7/1989 | Clements |
| 5,131,283 A | | 7/1992 | Canfield |
| 5,165,274 A | | 11/1992 | Thiercelin |
| 5,209,129 A | | 5/1993 | Jaselskis et al. |
| 5,246,862 A | | 9/1993 | Grey et al. |
| 5,323,648 A | | 6/1994 | Peltier et al. |
| 5,440,941 A | | 8/1995 | Kalidindi |
| 5,578,769 A | * | 11/1996 | Warrington et al. ..... 73/864.74 |
| 5,786,527 A | | 7/1998 | Tarte |
| 5,819,850 A | | 10/1998 | Lee, Jr. et al. |
| 5,889,217 A | | 3/1999 | Rossabi et al. |

* cited by examiner

*Primary Examiner*—Robert Raevis
(74) *Attorney, Agent, or Firm*—Dority & Manning, PA

(57) ABSTRACT

A cone penetrometer is provided having a pivoting arm which deploys a variable distance from the surface of the cone penetrometer. Sensors placed on the end of the deployable arm provide for data collection outside a compression zone created by the insertion of the cone penetrometer.

13 Claims, 3 Drawing Sheets

APPARATUS AND PROCESS FOR AN OFF-SURFACE CONE PENETROMETER SENSOR

This application claims the benefit of provisional application No. 60/160,975 filed Oct. 22, 1999.

STATEMENT OF GOVERNMENT RIGHTS

The United States Government has rights in this invention pursuant to Contract No. DE-AC09-96-SR18500 between the U.S. Department of Energy (DOE) and Westinghouse Savannah River Company.

FIELD OF THE INVENTION

This invention relates to a process and apparatus for subterranean monitoring and sensing subsurface parameters. More specifically, the invention relates to a cone penetrometer having a deployable sensor which is positionable away from the penetrometer surface. The extension of the sensor facilitates readings and data collection in a region outside the compression zone which forms upon deployment of a cone penetrometer.

BACKGROUND OF THE INVENTION

Contamination of subsurface soil and its environmental impact has been the subject of considerable public attention and has caused much concern with respect to the storage and disposal of waste materials given the potential for contamination. It is common for contaminants or hazardous materials to lodge in the interstices or pore space of the soil or to become part of the soil solutions, which can be generally defined as the interstitial water in the soil together with solutes and dissolved gases. Early detection and monitoring of such hazardous materials in subsurface soil solutions is critical so that problems can be addressed before a hazardous material or condition spreads. The need exists, therefore, for methods and apparatuses for obtaining accurate and representative samples of liquid and/or gas from subsurface soil. Further, absent any concern for hazardous materials, it is important and useful to be able to obtain subsurface samples for various other scientific purposes.

A common technique for subsurface site characterization utilizes a cone penetrometer system equipped with various sensors. The penetrometer system consists of a truck equipped with a vertical hydraulic ram that is used to force a rod with an umbilical cord into the ground at varying depths. It is known within the art to provide a suction device mounted near the rod to permit sample vapors from the soil to be transported via a tube for analysis such as a gas chromatograph coupled to a mass spectrometer. As the rod is pushed or retrieved from the ground, a vertical profile of soil conditions may be obtained. Repeated vertical profiling at various locations results in a three-dimensional mapping of a potentially contaminated site.

A variety of devices are known within the prior art for the sampling of subsurface soil and conditions. For instance, it is known in the art to use devices such as lysimeters which a vacuum pull-through conduit to draw soil solutions samples into a receptacle and through the conduit to the surface of the ground. For instance, U.S. Pat. No. 4,759,227 to Timmons, which is incorporated herein by reference, teaches an apparatus and process disclosing a lysimeter which utilizes a rigid, porous, fluoroplastic filter section through which soil moisture surrounding the lysimeter may be collected and introduced into a chamber of the lysimeter.

U.S. Pat. No. 5,035,149 to Yierenga discloses a lysimeter-type sampler having a tube-like porous stainless steel receptacle which permits entry of a subsurface solution. A second tube forms a non-porous stainless steel conduit is joined to the end of the first two. A series of alternating vacuum and pressure changes provides a pressure gradient for conveying the collected sample to the surface.

U.S. Pat. No. 5,209,129 to Jaselskis et al. discloses a subsurface sampler in which an outer cylindrical casing defines a series of portholes. The portholes are normally sealed during the insertion operation. Following insertion, an inner sleeve of the casing is partially rotated so that the portholes are exposed to the subsurface conditions. A tab or wiper is attached to the inner sleeve to clear a small space of blocking soil immediately alongside the outer surface of the casing.

U.S. Pat. No. 5,165,274 to Thiercelin discloses a down hole penetrometer which the penetrometer defines a tooth and an associated actuator for extending the tooth radially outward from the body so as to penetrate the wall of the bore hole. The arrangement is used to determine pore pressure prior to undertaking commercial drilling or hydraulic fracturing techniques.

U.S. Pat. No. 5,889,217 to Rossabi et al. discloses a cone penetrometer which is hydraulically pushed into the ground while in situ measurements are continually collected. The cone penetrometer provides a filtering zone in which samples of liquid and gas from subsurface oil may be collected and transported to the ground surface without having to return the apparatus itself to the surface.

One disadvantage of the above collection methods and apparatuses involves the substantial pressures required to insert the measuring device into the subsurface of the soil. Insertion of a cone penetrometer or similar structure creates compression zones in which the soil adjacent the penetrometer is compacted and undergoes other possible changes as a result of the compression pressure which results from insertion. As a result, it is by no means certain that measurements taken from within the compression zone accurately reflect the subsurface characteristics of the surrounding, non-compressed regions. Accordingly, there remains room for variation and improvement within the art.

SUMMARY OF THE INVENTION

The present invention is directed to a method and apparatus for positioning a sensor at a variable distance from the surface of a deployed cone penetrometer. It is a principal object of the present invention to provide an apparatus and method for positioning a below ground sensor outside a compression zone created upon the insertion of a cone penetrometer.

It is a further object of the present invention to provide a cone penetrometer having a pivoting arm which forms a portion of the exterior surface of the penetrometer. Upon deployment, the pivoting arm extends beyond the soil compression zone and facilitates the placement of a sensor on the terminal end of the deployed arm.

It is yet a further object of the present invention to provide a penetrometer having a deployable arm which may be extended variable distances from the surface of the penetrometer, thereby facilitating subsurface measurements both within and beyond a soil compression zone.

In accordance with the objects of the invention, the present sensor apparatus may obtain in situ measurements from a subsurface environment, the sensor apparatus having a tubular shaft having an exterior cylindrical wall and defining an interior cavity, the exterior wall further defining an opening; an arm being pivotally mounted via an axle which is operatively disposed within the tubular shaft, the arm being movable relative to the shaft between a closed position covering the exterior wall opening and a deployed position where a free end of the arm extends away from the surface of the tubular shaft; a motor disposed within the tubular shaft and in operative engagement with the axle; a sensor carried by the free end of the arm and in further communication with an interior of the tubular shaft; wherein, when the motor engages the axle, the axle is rotated and thereby pivots the arm from the closed position covering the shaft opening to a deployed position with the free end of the arm and the associated sensor positioned away from the exterior wall of the shaft.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

FIGS. 2A and 2B are sectional views of one embodiment of a cone penetrometer of the present invention setting forth details of a motor driven linkage system which provides deployment of the blade;

DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only and is not intended as limiting the broader aspects of the present invention, which broader aspects are embodied. in the exemplary constructions.

Figure 1:
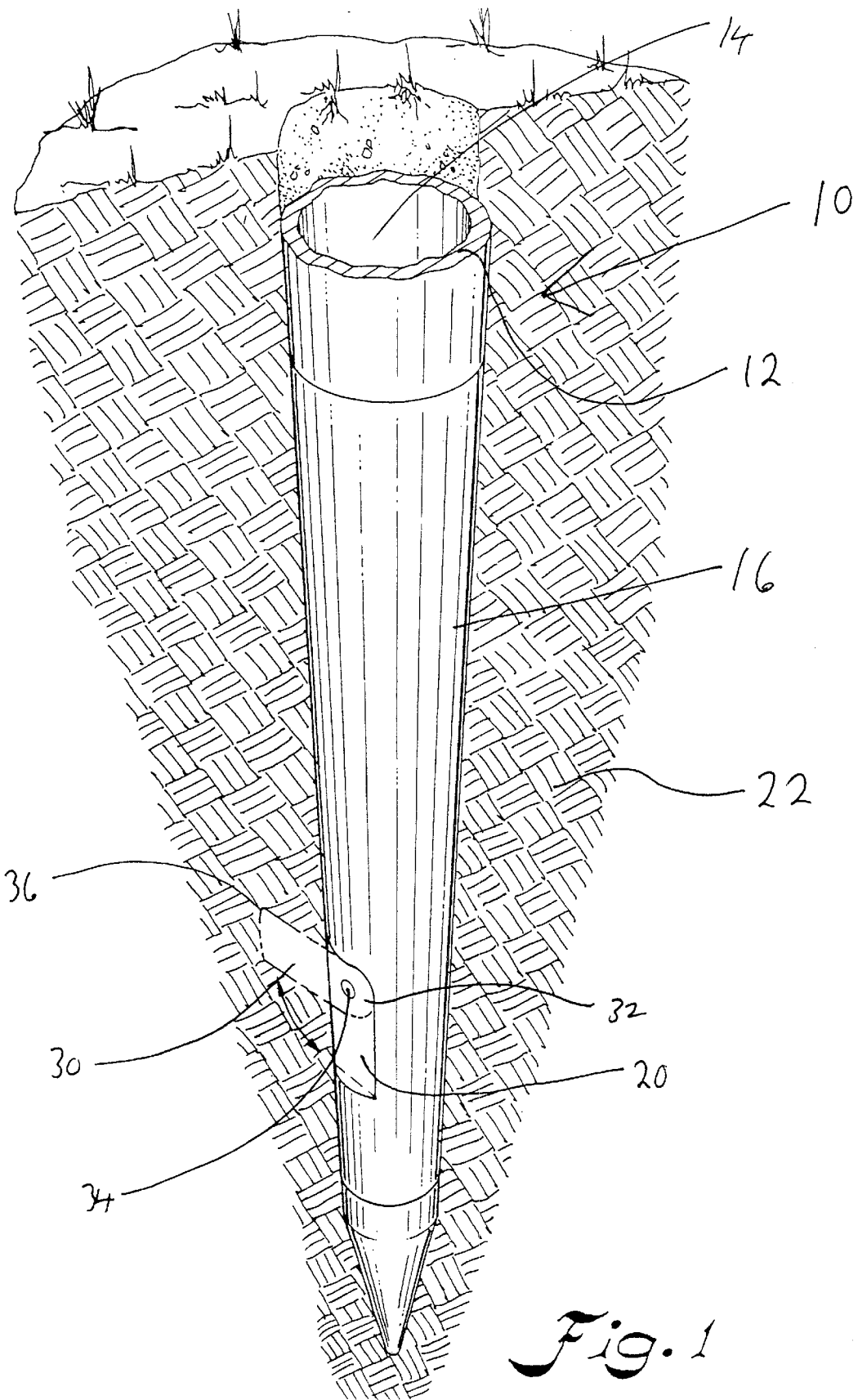
FIG. 1 is a perspective view of the present invention illustrating a deployed arm extending into the surrounding soil and away from the surface of the penetrometer.

As seen in reference to the Figures, a subsurface sensor apparatus is seen in the form of a cone penetrometer 10. Penetrometer 10 is defined in part by a cylindrical shaft 12 having a hollow interior 14 and an arcuate exterior cylindrical wall 16. As is conventional within the art, cylinder shaft 12 may be constructed from a tool grade or stainless steel. A rectangular opening 20 is defined within a segment of exterior wall 16, opening 20 providing access between the hollow interior 14 and a region of the surrounding subsurface 22 (FIG. 1).

Figure 2:
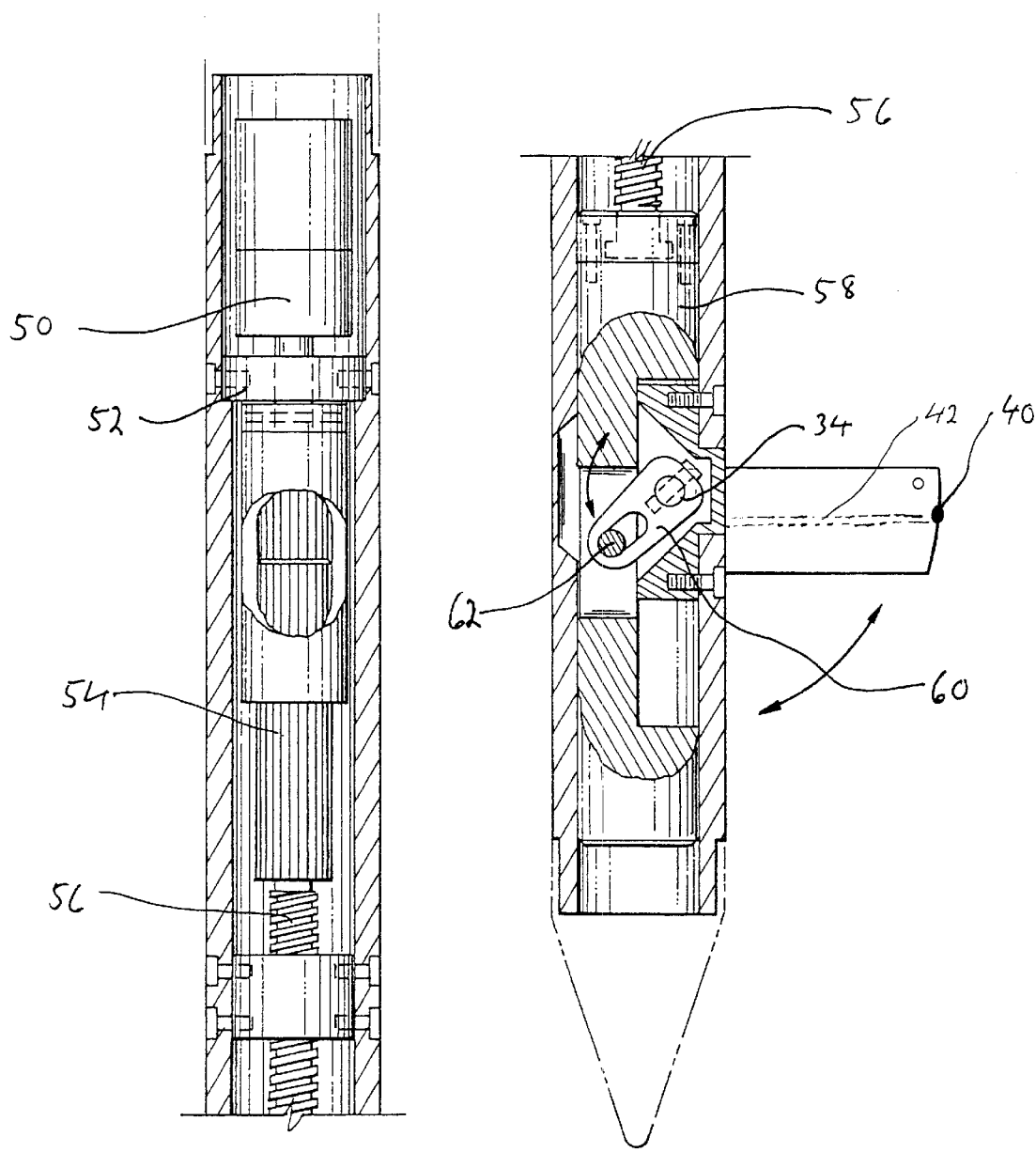
FIG. 2 is a schematic view illustrating the relative positions of the sectional views seen in FIGS. 2A and 2B.

An arm 30 is attached at one end 32 to a pivot 34 which is responsive to a gear or linkage mechanism housed within the interior 14 of shaft 12. It is best described below in reference to FIGS. 2A, 2B, and 3. Arm 30 is deployable about pivot 34 so that a free end 36 of arm 30 is positioned remote from the wall 16 and extends into the subsurface 22 at an approximate right angle relative to the initial flush position within opening 20. Arm 30 provides a blade-like structure which can be deployed within the subsurface 22. Arm 30 has a generally arcuate shape which conforms to both the size of opening 20 as well as the curvature of wall 16 and may be made of a high strength structural steel such as ASTM A514 carbon steel. The pivoting arm has a thin, blade-like profile and a generally arcuate shape which facilitates the motorized deployment of the blade from an initial flush position residing within opening 22 to a deployed position as seen in FIG. 1.

The deployed position of arm 30 preferably extends free end 36 to a maximum distance away from the surface of the cone penetrometer. When fully deployed, the free end 36 of arm 30 extends approximately 3 inches (7.6 cm) beyond the exterior wall 16 of cylindrical shaft 12. A sensor 40 is disposed upon the free end 36 of arm 30. While sensor 40 may be placed at various locations with respect to sensor arm 30, it is believed that placement on a terminal tip of arm 30 is the preferred sensor placement.

Sensor 40 may be selected from a wide variety of conventional sensors including temperature or resistivity sensors. Sensor 40 has one or more wires or other conduits 42 which extend along the arm 30 and into the interior 14 via opening 20. Conduit 42 may either be secured to an inner wall of blade 30 or extend through a drilled hole or other opening which extends through the length of arm 30. Both arrangements protect the sensor during the insertion of the penetrometer. If needed, the placement of the conduit 42 within the interior of arm 30 provides additional protection during deployment of arm 30 through subsurface soil 22.

It is envisioned that multiple arms may be present to allow for the deployment and use of multiple sensors. Further, multiple arms would facilitate the use of resistivity probes which conventionally use two probes, one for positive voltage and one for negative voltage. Such probes have each individual probe positioned on or within a separate arm or, alternatively, the arm itself, mounted on insulated bushings, could be used as one of the sensor probes.

The arm 30 is deployed by the use of reducer gears and a small electric motor. It is possible to achieve a gear design which will increase torque by a factor of 1,000 or greater and which can also be placed within the confined space of a penetrometer shaft. The actual design choice of a motor and gear system are not critical in that a number of different designs may be developed. One example of a suitable motor and gear design is seen in reference to FIGS. 2A and 2B where an electric motor 50 is held in a fixed position by a mounting bracket 52. The motor engages a spline 54 which further engages a screw member 56, undergoes axial movement during rotation with respect to spline 54. A terminus of screw member 56 is attached to a coupling 58 thereby permitting coupling 58 to be raised and lowered within the shaft interior 14. Pivot 34 of blade 30 engages a linkage 60 which is responsive to movement of a coupling member 58 via an intersecting pin 62. As coupling 58 is lowered, 10 pin 62 moves linkage 60 about a 90 degree rotation, thereby rotating pivot 34 90 degrees and fully deploying blade 30.

Figure 3:
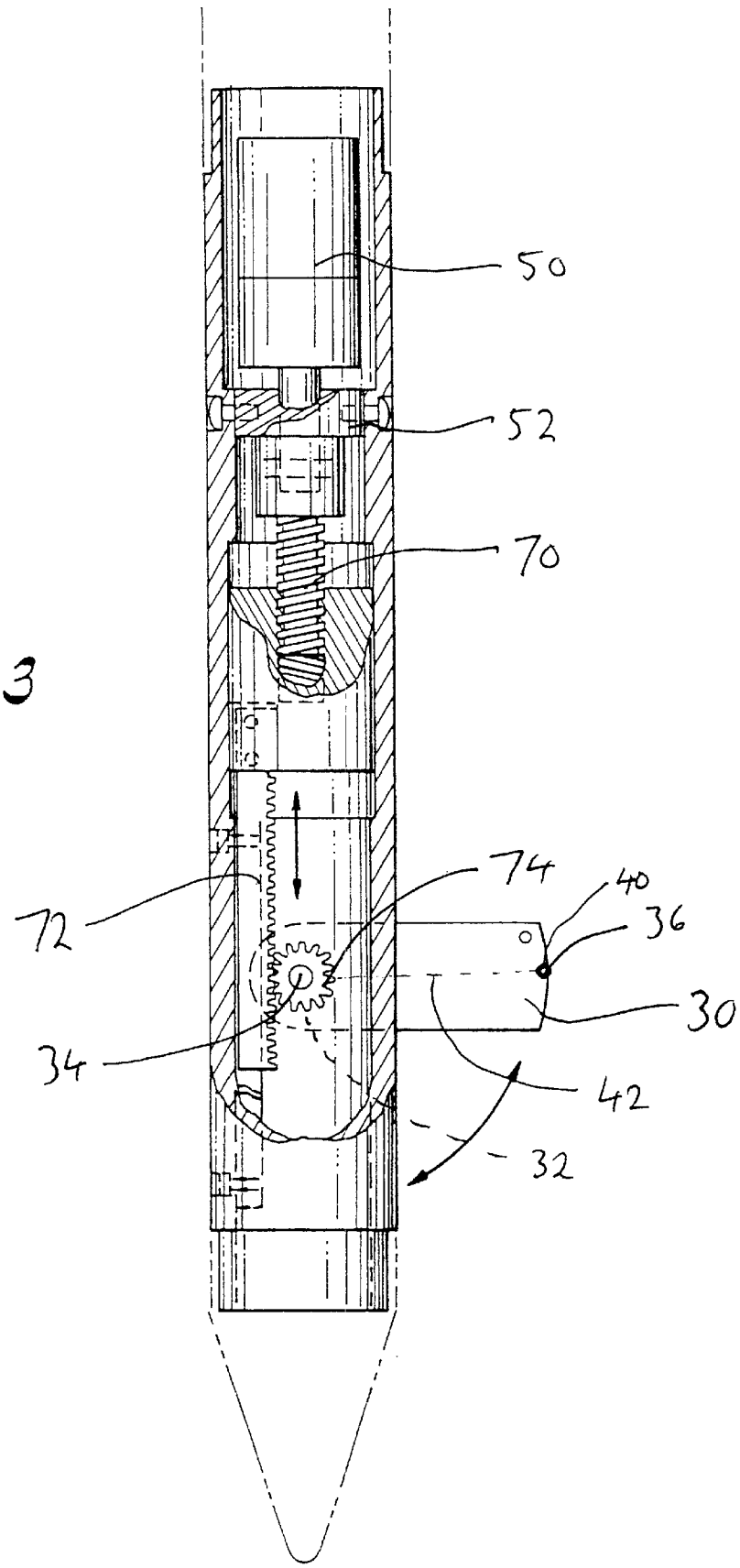
FIG. 3 is a sectional view of an alternative embodiment of a cone penetrometer motor driven gear rack to cause the rotation and deployment of the sensor arm.

An alternative embodiment of a motor and gear assembly for deploying blade 30 is seen in reference to FIG. 3. As seen in FIG. 3, a motor 50 is held in a fixed position within a shaft 14 by a mounting bracket 52. A screw 70 is used to raise and lower a gear rack 72, gear rack 72 being in further communication with a spur gear 74. Spur gear 74 is mounted adjacent an interior of blade 30 and engages pivot 34. In this manner, when the spindle of motor 50 is used to engage screw 70, gear rack 72 is correspondingly raised or lowered. In turn, spur gear 74 engages pivot 34 and thereby causes the deployment of arm 30.

As described in more detail below, motor 50 is operated in conjunction with either a magnetic or optical encoder as used which permits the use of various encoder counts to correlate with a position of deployment of arm 30. As a result, it is possible to select an intermediate position between a fully deployed arm and a fully retracted arm, thereby permitting sequential measurements across a compression zone. This ability will facilitate the collection of data and allow the termination of compression zone size within various soil types, the effects, if any, of a compression zone on various collected data, and whether a compression zone undergoes a timed recovery.

The control system which regulates the deployment of arm 30 is based on a DC electric motor 50 rating at 24 volts DC with a draw current not in excess of 3 A and a maximum continuous operating voltage not to exceed 55 volts DC. Other restrictions include those applicable to the National Semiconductor LMD 18201 H-Bridge circuit, National Instruments LM628/629 motion controller, and New Micros NMIS-7056 motion control card the uses of which are set forth below.

The illustrated embodiments make use of a DC operated motor with attached magnetic encoder and gear head. Optical encoders are also acceptable from a control system perspective but none have been found that meet the physical space limitations imposed on the motor and associated components. The motor, gear head, and encoder are all located in the very near proximity of the deployable arm 30. The motor control circuitry and power source are located remotely and connected to the motor and encoder via remote connecting cables. The motor, gear head, and encoder are selected based on mechanical size restrictions and required operating torque for a specific penetrometer system. As the piping size of different penetrometer systems varies, so will the requirements for maximum motor size and gear heads.

In order to operate the system, a control panel may be provided having a "retract arm", "extend arm", and/or "manual" command. The "retract" and "extend" commands have specific encoder counts (or encoder positions) associated with the commands that are predetermined and programmed into the system. The control system requests the desired encoder position as requested by the user command. The control system monitors and displays the progress toward meeting the target position. If the target position is achieved, then the control system declares the command successful. While the system is operating (either retracting or extending the arm) the control system monitors the current draw of the motor through a 0.2 ohm shunt resistor and associated amplifier circuit. If the current reaches a threshold limit, the control system shuts the motor operation down and declares a stall condition. A stall condition is defined as a state where the motor can not complete the desired position command without risking destruction of the motor and or physical linkage between the motor output and the shaft of the retractable blade. Also during blade extension or retraction the maximum current draw from the motor is monitored and displayed. Using calculated motor current versus torque curves it can be determined-the maximum force required to deploy in different types of soils at different depths. The "manual" command is available to allow the operator to specify a desired position (in encoder counts), deployment velocity, or deployment acceleration.

The control system utilizes a Motorola MC68HC11 embedded computer board with a motion control, 12 bit analog to digital, and serial communication peripheral cards. The motion control card is responsible for interfacing with and operation of the motor and encoder. The analog to digital card is responsible for monitoring current draw through the motor and for monitoring analog sensors that may be connected to the deployment arm. The serial communication card is used to transfer pertinent information through a serial port to either a connected thermal printer or attached personal computer. All software for the embedded controller system has been developed by the Engineered Equipment and Systems Department of Westinghouse Savannah River Company, Inc., and is stored in a permanent memory device on board the embedded controller card. The ability to develop similar software is well within the skill level of one having ordinary skill in the art.

Motor power and analog to digital reference voltage are supplied through two separate connectors on the back of the control box. This arrangement facilitates future design modifications that may require the use of a motor with different voltage and current requirements beyond the motor used in the initial design. Additionally, the analog to digital card may be operated at various reference voltages depending upon the requirements of the attached sensors.

Information is displayed to the user through two 4 line by 20 character LCDs. User input is accepted from a 20 character keypad with custom keys assigned for functions specific to the CPOSS operation. The CPOSS main control board operates from a 10 volt AC or DC source with approximately 20 milliamps of draw current. Collection data is stored on a data acquisition card. The acquisition card stores encoder counts versus current draw which permits the arm position to be determined versus motor torque during deployment and retraction. The data can be transferred from the data acquisition card to a host personal computer for incorporation in the subsequent analysis of measured parameters. With simple modifications, it is envisioned that the data can be transferred directly to the external personal computer for real-time transfer.

The opening 20 defined within the segment of exterior wall 16 helps facilitate the placement of the motor, encoder, and gear assembly components within the interior of the penetrometer cylinder. Depending upon the size and dimensions of opening 20, an additional access panel may be provided to facilitate the construction and assembly of the deployment components. Preferably, arm 30 is installed in a substantially flush configuration with the exterior surface of the cone penetrometer. In this manner, the flush configuration does not interfere with the insertion of the cone penetrometer.

The present invention offers several advantages over the prior art. Foremost, the deployable arm allows the positioning of a sensor at a predetermined distance from the exterior surface of the cone penetrometer. For instance, a deployment of a 3-inch arm is believed to afford a sensor location which avoids measurements within the compression zone. As such, the present invention allows the collection of data which more accurately reflects the subsurface region and its characterization.

Further, the present invention enables a sensor apparatus which can undertake a qualitative and quantitative analysis of a compression zone and a variety of different soil types. In this manner, it would be possible to characterize the type of data which may be altered by the formation of a compression zone by taking a series of measurements along the deployment pathway of arm 30. The encoded motor assembly allows accurate and controlled movement of the sensor arm which will facilitate characterization of the compression zone.

While the above described embodiments were described in reference to a rectangular arm 30, the size and shape of arm 30 may be varied according to site specific needs. For instance, the arm may be narrowed, elongated, or defined in alternative shape which may facilitate the deployment of the arm.

Preferably, the arm 30 maintains a generally arcuate profile matching a correspondingly shaped opening defined by the exterior wall of the penetrometer. The arcuate shape has been found to minimize the size of a secondary compression zone caused by the deployment of arm 30. By placement of the probe tip of sensor 40 along the terminal free edge and along a midpoint of the arcuate edge, the sensor placement avoids the secondary compression zone created by the deployment of arm 30.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. A sensor apparatus for obtaining in situ measurements from a subsurface environment comprising:
    a tubular shaft having an exterior cylindrical wall and defining an interior cavity, the exterior wall further defining an opening;
    an arm mounted via a pivot which is operatively disposed within the tubular shaft, the arm being movable relative to the shaft between a closed position covering the exterior wall opening and a deployed position where a free end of the arm extends away from the surface of the tubular shaft;
    a motor disposed within the tubular shaft and in operative engagement with the pivot;
    a sensor carried by a free end of the arm and in further communication with an interior of the tubular shaft;
    wherein, when the motor operably engages the pivot, the pivot is engaged and thereby moves the arm from the closed position covering the shaft opening to a deployed position with the free end of the arm and the associated sensor positioned away from the exterior wall of the shaft.

2. The sensor apparatus according to claim 1, wherein the arm is arcuate and is flush with the exterior wall when in the closed position.

3. The sensor apparatus according to claim 1 wherein when the arm is in a deployed position, the arm is substantially tangential to said exterior surface of the tubular shaft.

4. The sensor apparatus according to claim 1 wherein the motor operatively engages the pivot through a rack and pinion gear mechanism.

5. The sensor apparatus according to claim 1 wherein the motor engages a coupling attached to a linkage in communication with the pivot of the arm, the linkage undergoing a 90 degreee rotation and thereby positioning the arm to a deployed position.

6. The sensor apparatus according to claim 1 wherein when the arm is in a deployed position, the arm extends at about a right angle with respect to a longitudinal axis defined by said tubular shaft.

7. A process of positioning a sensor within a subsurface soil layer comprising:
    providing a penetrometer, the penetrometer having an exterior wall defining a blade and a free end of the blade having disposed thereon a sensor;
    inserting the penetrometer to a desired depth within a soil;
    pivoting the blade, thereby deploying a free end of the blade and the accompanying sensor to a soil region surrounding the penetrometer; and
    transmitting information from the sensor to the penetrometer.

8. A sensor apparatus for obtaining in situ measurements from a subsurface environment comprising:
    a tubular shaft having an exterior cylindrical wall and an interior, the exterior wall further defining an opening;
    an arm operatively disposed along the tubular shaft, the arm being movable relative to the shaft between a closed position covering the exterior wall opening and a deployed position wherein a portion of the arm extends away from the surface of the tubular shaft;
    a motor disposed within said interior of said tubular shaft and in operative engagement with said arm;
    a sensor carried by said portion of said arm, said sensor in further communication with an interior of the tubular shaft;
    wherein, when the motor operably engages the arm, the arm is moved from the closed position covering the exterior wall opening to a deployed position with the portion of the arm and the sensor positioned away from the exterior wall of the shaft.

9. The sensor apparatus according to claim 8, wherein the arm is arcuate and is flush with the exterior wall when in the closed position.

10. The sensor apparatus according to claim 8 wherein when the arm is in a deployed position, the arm extends at about a right angle with respect to a longitudinal axis defined by said tubular shaft.

11. The sensor apparatus according to claim 8 wherein the motor operatively engages the arm through a rack and pinion gear mechanism.

12. The sensor apparatus according to claim 8 wherein the motor engages a coupling attached to a linkage in communication with the arm, a movement of the linkage thereby extending the arm to a deployed position.

13. A process of positioning a sensor within a subsurface soil layer comprising:
    providing a penetrometer, the penetrometer having an exterior wall defining a blade and an extendable portion of the blade having disposed thereon a sensor;
    inserting the penetrometer to a desired depth within a soil;
    pivoting the blade, thereby deploying said extendable portion of the blade and the accompanying sensor to a soil region surrounding the penetrometer; and
    transmitting information from the sensor to the penetrometer.

* * * * *